(12) United States Patent
Ebert et al.

(10) Patent No.: US 8,882,664 B2
(45) Date of Patent: Nov. 11, 2014

(54) ANIMAL SYMPTOM VISUAL ANALYTICS

(75) Inventors: David S. Ebert, West Lafayette, IN (US); Ross Larry Maciejewski, Phoenix, AZ (US); Benjamin N. Tyner, Charlotte, NC (US); Yun Jang, West Lafayette, IN (US); William Cleveland, Lafayette, IN (US); Sandra Amass, Lafayette, IN (US)

(73) Assignee: Purdue Research Foundation, West Lafayette, IN (US)

( * ) Notice: Subject to any disclaimer, the term of this patent is extended or adjusted under 35 U.S.C. 154(b) by 272 days.

(21) Appl. No.: 13/190,748

(22) Filed: Jul. 26, 2011

(65) Prior Publication Data

US 2012/0035429 A1     Feb. 9, 2012

Related U.S. Application Data

(63) Continuation-in-part of application No. 12/286,756, filed on Oct. 1, 2008, now abandoned.

(60) Provisional application No. 60/997,150, filed on Oct. 1, 2007.

(51) Int. Cl.
| | |
|---|---|
| *A61B 5/00* | (2006.01) |
| *G06F 7/60* | (2006.01) |
| *G06F 17/10* | (2006.01) |
| *G06F 19/24* | (2011.01) |
| *G06F 19/00* | (2011.01) |
| *G06F 19/26* | (2011.01) |

(52) U.S. Cl.
CPC ............ *G06F 19/3493* (2013.01); *G06F 19/24* (2013.01); *G06F 19/26* (2013.01); *G06F 19/3487* (2013.01)
USPC .............................................. 600/300; 703/2

(58) Field of Classification Search
CPC ............ G60F 17/5009; G60F 17/5018; G60F 17/5036; G60F 2217/19; G06T 17/00; G06T 17/10; G06T 17/20; G06T 17/005; G06T 19/00; G06T 15/00; G06T 15/10; G06Q 10/10; G06Q 40/08; G06Q 50/22; G06Q 50/24; G06Q 19/322
USPC ....................... 703/2; 345/419–420; 705/2–3; 717/104–113
See application file for complete search history.

(56) References Cited

U.S. PATENT DOCUMENTS 6,714,925 B1 * 3/2004 Barnhill et al. ................. 706/48
7,050,933 B2 * 5/2006 Parvin et al. .................. 702/179

(Continued)

OTHER PUBLICATIONS

USGS—West Nile Mosquito Incidences 2006 Local—California Cumulative Mosquito Infections http://diseasemaps.usgs.gov/2006/wnv_ca_mosquito.html map and data archives for annual cumulative counts date back to Sep. 23, 2006.*

(Continued)

*Primary Examiner* — William Thomson
*Assistant Examiner* — Shirley Jian
(74) *Attorney, Agent, or Firm* — Maginot, Moore & Beck, LLP (57) ABSTRACT

A system and method for visually displaying and analyzing public health data for geospatial and/or time variations, including the collection of symptom data coupled with geographic and time data, filtering the symptom data based upon a selected time period and geographic range, and creating a visual result based upon statistical modeling including power transform and/or data normalization. According to at least one embodiment, the system for visually displaying and analyzing includes selecting and performing at least one aberration detection method such as applying CUSUM analysis, quantile measures, and/or bootstrapping analysis, and displaying the result to a user via a visual analytics arrangement.

12 Claims, 6 Drawing Sheets

(56) References Cited

U.S. PATENT DOCUMENTS

| | | | | |
|---|---|---|---|---|
| 7,457,731 | B2* | 11/2008 | Rao | 703/2 |
| 2003/0101012 | A1* | 5/2003 | Parvin et al. | 702/84 |
| 2003/0177038 | A1* | 9/2003 | Rao | 705/2 |
| 2004/0236604 | A1* | 11/2004 | McNair | 705/2 |

OTHER PUBLICATIONS

USGS—Final 2006 West Nile Virus Human Neuroinvasive Disease Incidence in the United States http://www.cdc.gov/ncidod/dvbid/westnile/mapsincidence/surv&control06IncidMaps.htm.*

* cited by examiner

ANIMAL SYMPTOM VISUAL ANALYTICS

PRIORITY

This application is a continuation-in-part of U.S. patent application Ser. No. 12/286,756 to Ebert et al. and entitled "Linked Animal-Human Health Visual Analytics, filed Oct. 1, 2008, which claims the benefit of U.S. Provisional Patent Application Ser. No. 60/997,150, filed Oct. 1, 2007, both of which are incorporated herein by reference.

This invention was made with Government support under NA/IND20768 awarded by USDA/NIFA. The Government has certain rights in the invention.

FIELD OF THE INVENTION

The present invention relates generally to visual analytic tools, and more particularly, to visual analytic tools used in the field of public health.

BACKGROUND OF THE INVENTION

The role of public health surveillance is to collect, analyze and interpret data about biological agents, diseases, and other health events in order to provide timely dissemination of collected information to decision makers. Surveillance activities share several common practices in the way data is collected, managed, transmitted, analyzed, accessed and disseminated. A type of surveillance known as syndromic surveillance can be used for early detection disease outbreaks based on symptoms and human behavior.

It is also known that monitoring diseases and health conditions in companion animal populations can provide early warning signs for emerging diseases, and some studies estimate that as much as 73% of emerging infectious diseases are zoonotic in origin. Companion animals can also provide warnings of possible exposure to pollutants, chemicals, allergens and natural toxins. In particular, such substances originate from the living environment and can have a detrimental effect on animal health as well as human health. If animal health issues manifest earlier than humans, then health care officials may be able to identify possible a toxin pollution event based on animal health monitoring before significant human effects are evident, particularly in light of the privacy concerns with human health data that often results in the obfuscation of time and/or location specifics with symptoms.

However, the raw data relating to human symptoms and/or animal symptoms for public health surveillance can be difficult to assess. Software-based visual analytic tools have been introduced to provide displays of the symptom data in an intuitive way that may be used to identify problem areas, and may include visual analytic tools. The goal of such tools is to provide an intuitive overview of large amounts of data, preferably with the ability to drill down into the data and/or perform additional statistical analysis on select portions of the data.

In the field of health surveillance, a user may view instances of gastrointestinal illness symptoms over a particular area for various times during the year, noting times of year and/or areas when the gastrointestinal illness symptoms occurred in seemingly larger quantities. The user may then perform statistical analysis to determine further information about those specific instances. However, those systems are not capable of both high true positive rates (precision) and low false positive rates (recall).

It has been known in the past to generate visual tools that provide at least some animal health and human health information based on occurrences of detected symptoms. However, many of the display and aberration detection techniques applicable to human symptoms cannot be usefully applied to animal symptom data. Further, as noted above, much of the data collected for human symptoms is often encumbered by privacy concerns, being collected only on the Zip Code level, and is often not being collected on a real-time basis. In addition, the methods used for syndromic surveillance in human data are not necessarily applicable to syndromic surveillance in animal data. Accordingly, there is a need for improved techniques of generating and displaying visual analytics of animal symptoms for public health surveillance purposes.

SUMMARY

At least some embodiments of the present invention [incorporating claim language upon approval].

The above-described features and advantages, as well as others, will become more readily apparent to those of ordinary skill in the art by reference to the following detailed description and accompanying drawings.

DETAILED DESCRIPTION

Figure 1:
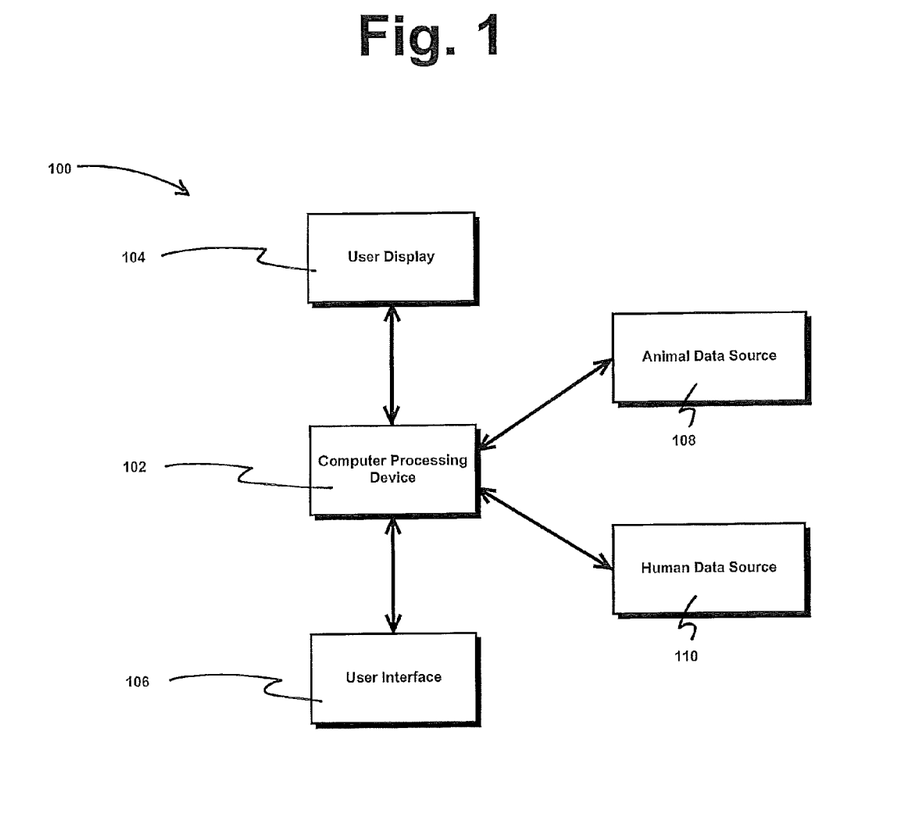
FIG. 1 shows a diagrammatic representation of a visual analytics arrangement according to an exemplary embodiment of the invention.

FIG. 1 shows a diagrammatic representation of a visual analytics arrangement 100 according to an exemplary embodiment of the invention. The visual analytics arrangement 100 includes a computer processing and storage device 102 coupled to a user display 104, a user interface 106, an animal data source 108 including animal symptom data, and a human data source 110 including human symptom data. The computer processing and storage device 102 may be any suitable work station, portable computer, or similar device. According to certain exemplary embodiments, computer processing and storage device 102 includes a network connection 112 that facilitates connection to one or more animal data sources 108 and/or one or more human data sources 110.

User display 104 is any visual display, and may suitably comprise a display integral to or configured for the computer processing and storage device 102. Similarly, the user input device 106 may include any and all input devices normally associated with computer processing and storage devices, and indeed may comprise devices integrally packaged with the computer processing and storage device 102.

Animal data source 108 is a source of reported companion animal symptoms coupled to a geographic location. For instance, according to at least one exemplary embodiment, animal data source 108 is a reported list of symptoms observed in a veterinary clinic located in a geographical area of interest or for all areas in which the data is available. By way of nonlimiting example, one current source of such data is a database for the Banfield Pet Hospital network, a network that provides nationwide coverage with demographics distributed according to human population density. Coverage of the Banfield Pet Hospitals is approximately one location for every five-mile radius containing 100,000 pet owners. However, it will be appreciated that other animal data sources 108, including those of localized animal health clinics, may be utilized. Likewise, another source of potential data is pharmacy or pharmaceutical company sales data within particular geographic areas.

Human data source 110 is any source of human health complaints, such as a local patient care data network that logs and records emergency room visits for multiple hospitals in an area of interest. By way of nonlimiting example, one current source of such data is a database for Indiana Network for Patient Care, a patient database utilized within the Indiana region. However, it will be appreciated that other human data sources 110, including localized, regionalized, and/or nationalized hospital, emergency room, and/or patient reporting sources may be utilized.

In general, visual analytics arrangement 100 displays information regarding public health in a manner that provides for intuitive analysis, using geospatial and/or temporal maps. Geospatial and/or temporal maps provide a geographical map of an area of interest, and may provide glyphs or other visual symbols to indicate locations, timing, and/or frequency of phenomena. In accordance with this embodiment of the present invention, the arrangement 100 provides, among other things, a geospatial and/or temporal map that shows the number and location of animals (and, if selected, human) with selected health symptoms reported in animal data source 108. Additional details regarding the displays generated by the arrangement 100 are provided further below.

Figure 2:
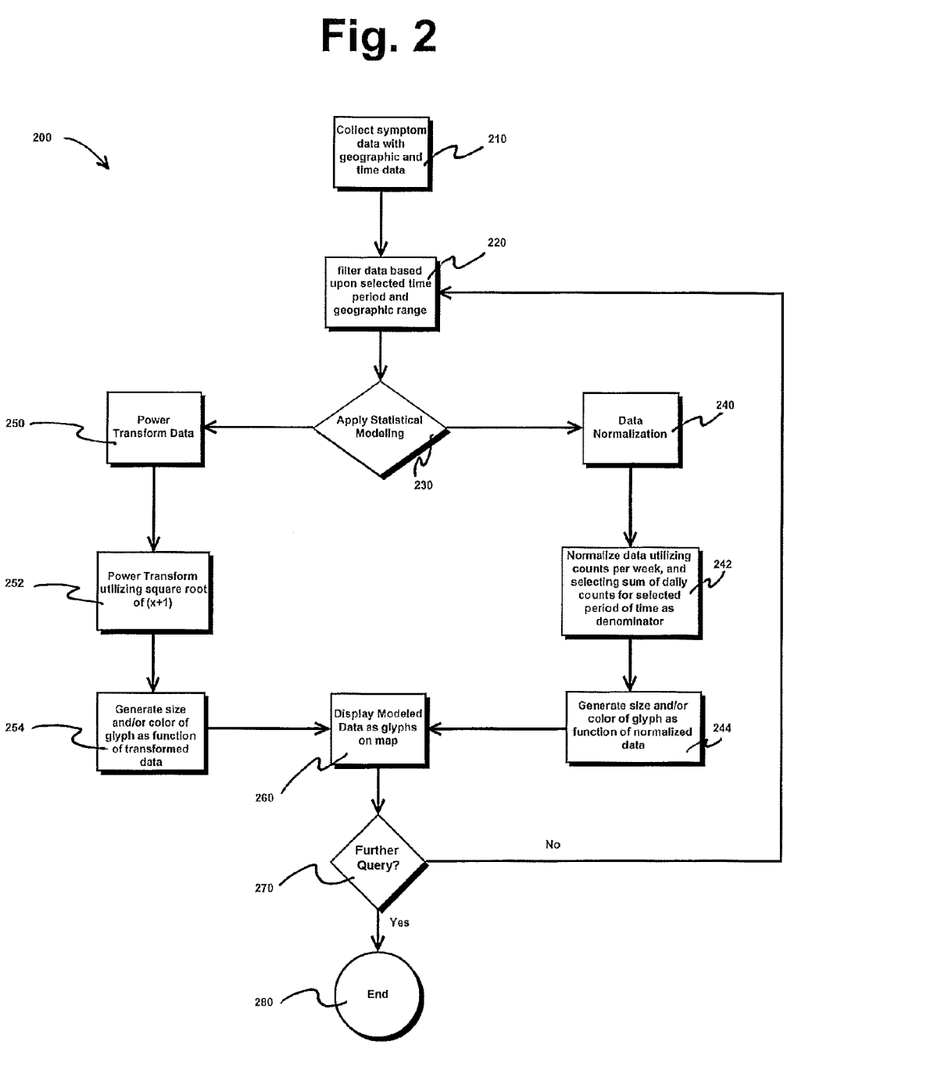
FIG. 2 shows a flow diagram of an exemplary set of operations that may be carried out by a computing device to generate a geospatial and/or temporal display of the visual analytics arrangement of FIG. 1.

FIG. 2 shows an exemplary embodiment of a method for analyzing geospatial and/or temporal data display utilizing a visual analytics arrangement. According to at least one embodiment, the method for analyzing geospatial and/or temporal data 200 includes the steps of: collecting symptom data 210; filtering that symptom data based upon selected parameters 220; applying statistical modeling 230 to the symptom data based upon the selected time period and geographic range; and displaying the modeled data as glyphs on a geographic display such as a map 260.

According to at least one embodiment, the step of applying statistical modeling 230 includes the use of logarithm or power transformation, such as a power transformation step 250. Further, according to at least one embodiment, the use of a logarithm or power transformation includes a step 252 of performing a power transform utilizing the square root of (x+1) for a given time period and geographic range. Similarly, depending upon the data supplied, the log(x+1) or a simple square root transformation could be utilized, depending upon the variability of the data. Upon applying the power transformation or logarithm, visual analytics arrangement 100 performs step 254 of generating a glyph having a size and/or color driven by the function of the transformed data. Thereafter, the statistically modeled data is displayed to a user via visual analytics arrangement 100 by displaying the glyphs generated in step 254 on a map in the geographic location associated with the data 260.

According to at least one other embodiment, the step of applying statistical modeling 230 includes the use of data normalization as shown in step 240. According to at least one embodiment, step 240 of normalizing data is performed, for example, to reduce the variation caused by seasonal effects and increases in data collection capacity. According to at least one embodiment, step 240 of normalizing data may include step 242 of utilizing counts per week for each of one or more particular locations to compensate for different scaling in counts over time. Further, according to at least one embodiment, generating a normalized value for each of one or more locations is performed by dividing the total value for each of the plurality of locations by a total number of reported symptom incidences for a corresponding site over a time window. By way of nonlimiting example, the denominator of such a normalization in step 242 utilizes the sum of the daily counts for the past month, two months, three months, four months, five months, six months, seven months, eight months, nine months, ten months, eleven months, or year. The use of a sliding window normalizing data utilizing counts per week allows observation of seasonal effects and larger trends while removing smaller aberrations and intra-week sampling effects. However, it will be appreciated that such a sliding window normalization will not be utilized when a user wishes to observe short-term effects.

According to at least one exemplary embodiment, upon performing data normalization through steps 240 and 242, in step 244 the normalized data is utilized to generate glyphs of a size and/or color as a function of the normalized data generated in steps 240 and 242. Thereafter, in step 260, the generated glyphs are displayed to a user via visual analytics arrangement 100 on a map in the geographic location associated with the data.

Upon review of the glyphs generated and displayed on the map in step 260, in step 270, a user evaluates the display to determine whether the generated display is acceptable for the user's evaluative purposes, or whether further querying would be preferred. If the display provides the requisite information needed for the user's evaluative purposes, the user may utilize the display as generated, and may print, save, or otherwise share, either physically or digitally, the results with colleagues for reporting purposes, for generating discussion on the findings, or for other uses. However, should the display fail to provide the requisite information, should another time period or evaluative method be needed, or should the results cause the user to determine that additional querying is necessary, the user may re-start the method for analyzing geospatial and/or temporal data display 200 from any of the prior steps such as step 210 of collecting additional data, step 220 of filtering the data based upon a selected time period and geographic range 220, step 230 of applying statistical modeling, or any other step deemed necessary by the user.

Figure 3:
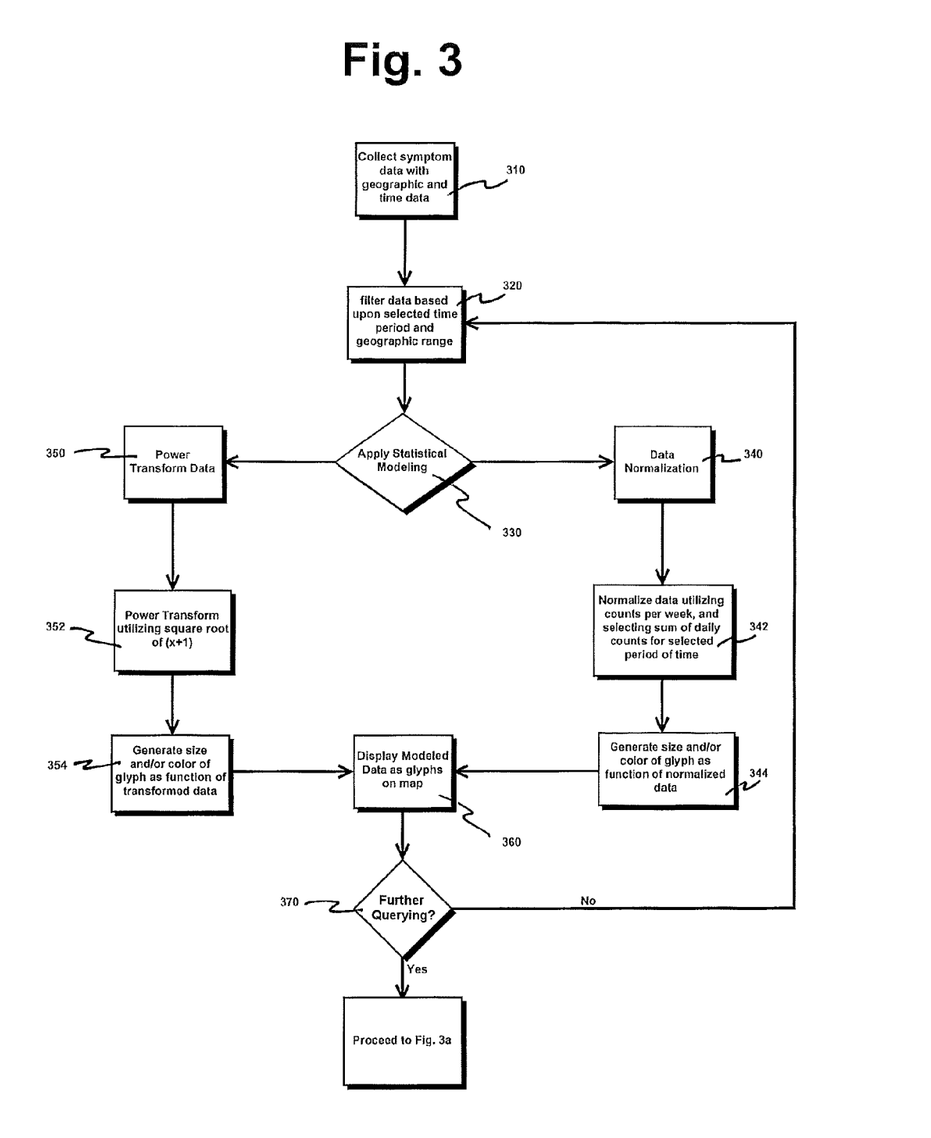
FIGS. 3 and 3a shows a flow diagram of an exemplary set of operations that may be carried out by a computing device to generate a refined analysis of the raw geospatial and/or temporal display of the visual analytics arrangement of FIG. 1.
Figure 3A:
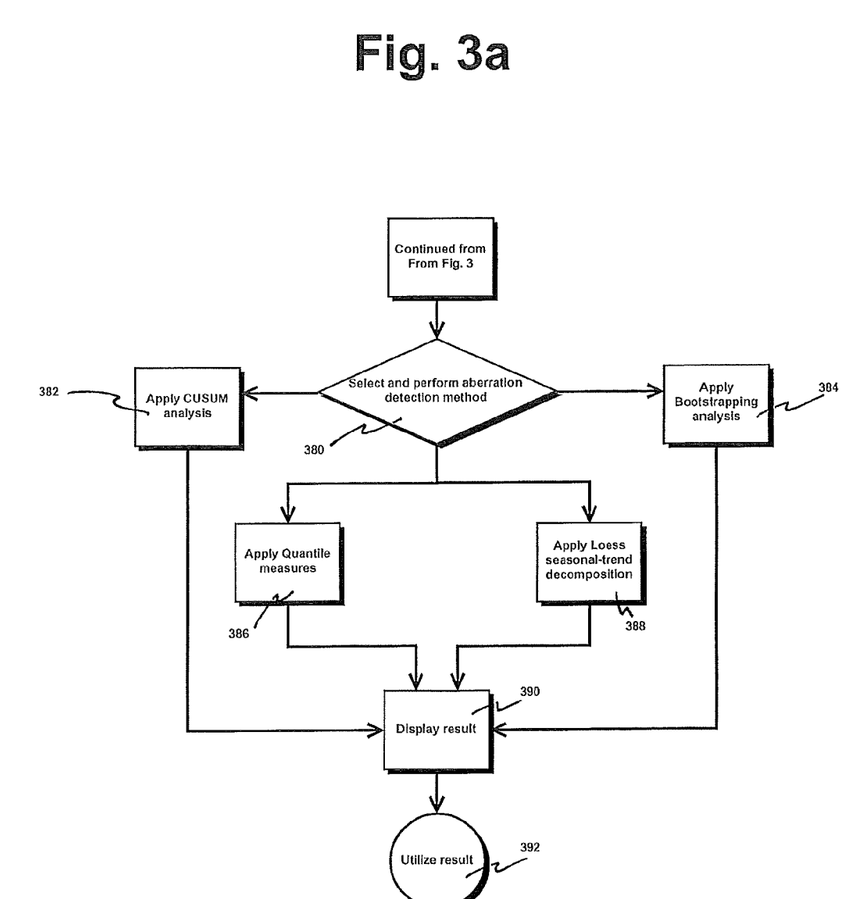

Turning now to FIGS. 3 and 3a, according to at least one exemplary embodiment of a method for analyzing geospatial and/or temporal data display utilizing a visual analytics arrangement 300, including the steps of: collecting symptom data 310; filtering that symptom data based upon selected parameters 320; applying statistical modeling 330 to the symptom data based upon the selected time period and geographic range; and displaying the modeled data as glyphs on a geographic display such as a map 360.

According to at least one embodiment, the step of applying statistical modeling 330 includes the use of logarithm or power transformation, such as a power transformation step 350. Further, according to at least one embodiment, the use of a logarithm or power transformation includes a step 352 of performing a power transform utilizing the square root of (x+1) for a given time period and geographic range. Similarly, depending upon the data supplied, the log(x+1) or a simple square root transformation could be utilized, depending upon the variability of the data. Upon applying the power transformation or logarithm, visual analytics arrangement 100 performs step 354 of generating a glyph having a size and/or color driven by the function of the transformed data. Thereafter, in step 360, the statistically modeled data is displayed to a user via visual analytics arrangement 100 by displaying the glyphs generated in step 354 on a map in the geographic location associated with the data 360.

According to at least one other embodiment, the step of applying statistical modeling 330 includes the use of data normalization as shown in step 340. According to at least one embodiment, step 340 of normalizing data is performed, for example, to reduce variation and data noise. According to at least one embodiment, step 240 of normalizing data may include step 342 of utilizing counts per week for each of one or more particular locations to compensate for different scaling in counts over time. Further, according to at least one embodiment, generating a normalized value for each of one or more locations is performed by dividing the total value for each of the plurality of locations by a total number of reported symptom incidences for a corresponding site over a time window. By way of nonlimiting example, the denominator of such a normalization in step 342 utilizes a sum of the daily counts for the past month, two months, three months, four months, five months, six months, seven months, eight months, nine months, ten months, eleven months, or year for such normalization. The use of a sliding window normalizing data utilizing counts per week allows observation of seasonal effects and larger trends while removing smaller aberrations and intra-week sampling effects. However, it will be appreciated that such a sliding window normalization will not be utilized when a user wishes to observe short-term effects.

Upon performing data normalization through steps 340 and 342, in step 344, the normalized data is utilized to generate glyphs of a size and/or color as a function of the normalized data generated in steps 340 and 342. Thereafter, in step 360, the generated glyphs are displayed to a user via visual analytics arrangement 100 on a map in the geographic location associated with the data.

Upon review of the glyphs generated and displayed on the map in step 360, in step 370, a user evaluates the display to determine whether the generated display is acceptable for the user's evaluative purposes, or whether further querying would be preferred. If the display provides the requisite information needed for the user's evaluative purposes, the user may utilize the display as generated, and may print, save, or otherwise share, either physically or digitally, the results with colleagues for reporting purposes, for generating discussion on the findings, or for other uses. However, should the display fail to provide the requisite information, should another time period or evaluative method be needed, or should the results cause the user to determine that additional querying is necessary, the user may re-start the method for analyzing geospatial and/or temporal data display 300 from any of the prior steps such as step 310 of collecting additional data, step 320 of filtering the data based upon a selected time period and geographic range 320, step 330 of applying statistical modeling, or any other step deemed necessary by the user.

According to at least one embodiment, in at least one additional step, once a user is satisfied with the results of the statistically modeled data, or in lieu of utilizing the statistically modeled data a user may select and perform at least one aberration detection method in step 380.

According to at least one embodiment, a user may utilize the step of performing a CUSUM analysis for the at least one aberration detection method as shown in step 382. For purposes of this nonlimiting example, CUSUM is defined as:

$$S_t = \max\left(0, S_{t-1} + \frac{x_t(\mu_0 + k\sigma_{x_1})}{\sigma_{x_1}}\right)$$

where $S_t$ is the current CUSUM, $S_{t-1}$ is the previous CUSUM, $X_t$ is the count at the current time, $\mu_0$ is the expected value, $\sigma_{X_t}$ is the standard deviation, and k is the detectable shift from the mean. $\mu_0$ and $\sigma_{X_t}$ are computed according to the degree of sensitivity. According to at least one embodiment, a user may define three different models (C1, C2, C3), with each model utilizing different time period for the $\mu_0$ and $\sigma_{X_t}$ computations. By way of nonlimiting example, C1 is the baseline period is $Day_{-7}, \ldots, Day_{-1}$ and a flag is noted on $Day_0$. Further, by way of nonlimiting example, C2 uses $Day_{-9}, \ldots, Day_{-3}$ as the baseline, and C3 uses $Day_{-9}, \ldots, Day_{-3}$ as the baseline. Further, according to at least one embodiment, an average of $Day_{-2}, \ldots, Day_0$ is used to detect the aberration. It will be appreciated that in at least one embodiment, in the event that the symptom data has a relatively small number of counts, doubled baselines may be utilized in order to avoid zero count for the baseline period.

According to at least one embodiment, a user may utilize the step of performing a bootsrapping analysis for the at least one aberration detection method as shown in step 384. It will be appreciated that bootstrapping is a general-purpose robust alternative to parametric inference used when the analyst does not wish to make strong parametric assumptions about the data. According to at least one embodiment, bootstrapping involves the sampling of data with replacement in order to simulate the distribution of the data and functions thereof. According to at least one nonlimiting example a user applying bootstrapping to dependent data will preserve as much of the dependence structure as possible when doing the resampling, typically through a blocked approach.

It will be appreciated that the step of applying bootstrapping analysis 384 is computationally intensive, but, according to at least one embodiment, may be employed in a straight-forward manner. Specifically, according to one exemplary embodiment, to obtain R null replicates of the statistic, resampling R windows of length $t_w$ days corresponding to null data and computing the statistic may result in bootstrap replicates $S_t^{(1)}, S_t^{(2)}, \ldots, S_t^{(R)}$. According to at least one embodiment, in prospective mode, the null data occurs prior to the window under investigation; in retrospective mode, one may opt to include data from after the window as well. According to at least one embodiment, the bootstrap significance associated with S* is then $$p_t = (1 + \text{number of } \{S_t^{(i)}\} \text{ exceeding } S_t^*)/(1+R)$$

If the mild assumptions underlying the bootstrap hold, the nun distribution of $p_t$ is approximately discrete uniform over $\{1/R, 2/R, \ldots, R/R\}$. Consequently, if there is no signal in the window under investigation, rejecting the null hypothesis when $p_t^* \leq \alpha$ will result in a false alarm rate of $\alpha \times 100\%$. According to at least one embodiment, in prospective mode, a system may update pt with the passage of time, and in this case a plot of $p_t^*$ versus $_t$ may be appropriate. In this case the $\{p_t\}$ are themselves correlated; moreover, the probability of at least one false alarm grows with $_t$ for fixed $\alpha$. If the number of null windows is less than R (common for our analyses), then bootstrapping is unnecessary when only a p-value is required, since the bootstrap p-value will have expectation equal to the fraction of null windows with statistic at least as extreme as the observed value.

According to at least one embodiment, a user may utilize the step of performing a quantile measures for the at least one aberration detection method as shown in step 386. By way of nonlimiting example quantile measures may be utilized to detect unusual variation in symptomatic data when operating in retrospective mode. According to at least one embodiment, quantile measures may be performed by selecting all data within a radius of incidence, identifying all symptomatic encounters over a time window of $t_w$ days after the alleged release at time t. Over the window $[t, (t+t_w)]$, there is a distance to the epicenter associated with each symptomatic encounter, and the detection statistic $S^*_t$ is the radius inside which x % of the window's symptomatic cases occur. As such, quantile measurement operates on the theory that an adverse event near the epicenter will cause the distribution of these distances to be shifted downward, and this particular aberration detection method utilizes this theory detect such shifts over time.

Yet another aberration detection method includes seasonal-trend decomposition based on loess, as shown in step 388. Such an aberration detection method results in signal correlation. By way of nonlimiting example, time series signals may be viewed as the sum of multiple trend components: a seasonal component and remainders. According to at least one embodiment, for each data signal, "trend components" are extracted to represent the long term trend and yearly seasonality using a seasonal decomposition of time series by loess ("STL"). In such an example, the "seasonal component" would represent the day-of-the-week effect as expressed in the following equation:

$$Y_{it} = T_{it} + S_{it} + D_{it} + r_{it}$$

where for the ith series, $Y_{it}$ is the original series, $T_{it}$ is the long term trend, $S_{it}$ is the yearly seasonality, $D_{it}$ is the day-of-the-week effect, and $r_{it}$ is the remainder. Such an exemplary example allows the correlation between the extracted components to be analyzed for any potential effects on one another.

According to at least one embodiment, after the step of selecting and performing aberration detection methods has been utilized, the generated data is visually displayed to a user via visual analytics arrangement 100 in step 390. Upon review of the data generated and displayed in step 390, according to at least one embodiment, a user can evaluate the display to determine whether the generated display is acceptable for the user's evaluative purposes. If the display provides the requisite information needed for the user's evaluative purposes, the user may utilize the display as generated, and may print, save, or otherwise share, either physically or digitally, the results with colleagues for reporting purposes or for generating discussion on the findings. However, should the display fail to provide the requisite information, or should another time period or evaluative method be needed, the user may re-start the method for analyzing geospatial and/or temporal data display 300 from any of the prior steps and/or may change the parameters, statistical modeling methods, and/or aberration detection steps to reach a desired outcome.

Example 1

Figure 4:
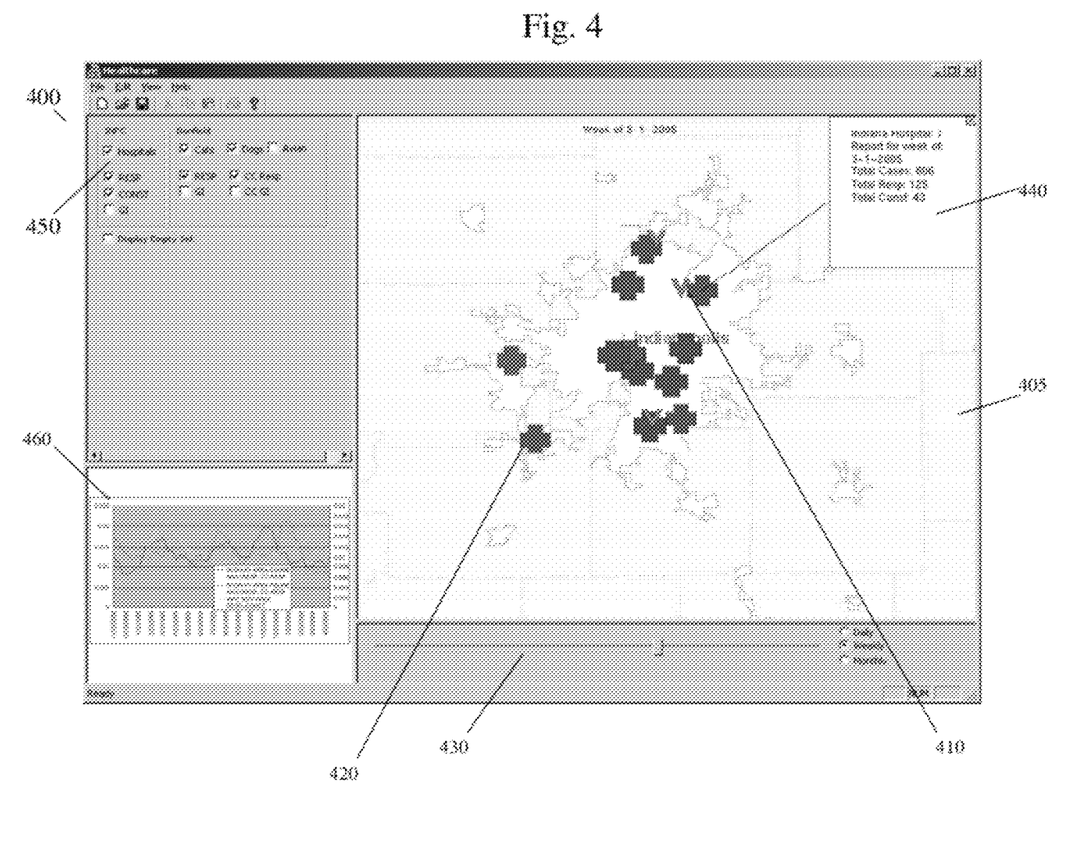
FIGS. 4 and 4a shows an exemplary display generated by the visual analytics system carrying out the operations of FIGS. 2 and/or 3.

According to at least one exemplary embodiment, a visual analytics system utilizes both data-management and statistical modeling embodiments discussed above. For instance, an initial direct access query may be made to a database is made, and human hospitals, veterinary hospitals, and individual animal locations are displayed on an interactive map such as that shown in FIG. 4. As shown in FIG. 4, at least one exemplary embodiment includes a visual display of a the geo spatial rendition of temporal data 400 for a selected syndrome or symptom displaying generated glyphs signifying normalized or power transformed data of both veterinary hospital and emergency room data.

In particular, in FIG. 4, veterinary hospitals 410 are depicted by a "V", cats are depicted by a triangle (not shown), dogs are depicted by circles (not shown), and emergency rooms 420 are depicted by crosses. According to at least one exemplary embodiment, for a selected syndrome, the size and color of the visual depictions directly relate to the number of cases seen within a selected time period, normalized by either a six-month sliding window as discussed above, or through a power transformation. For example, according to at least one embodiment, as more cases of a particular syndrome are encountered during the specified time period, the glyph color changes from green to red, and the glyph area increases proportionally to the number of cases. According at least one exemplary embodiment, glyph scaling may be set smaller for higher specificity or larger to help signal alerts. Further, the time period may be specified as daily, weekly, or monthly using user-input controls such as a sliding scale 430, allowing a user to move forward and backwards through time. Further, as discussed above, each glyph may be selected to show details regarding the reported data in a detail box 440.

According to at least one embodiment, further information may be obtained regarding a given glyph by selecting that glyph via a user interface and a data selection interface 450, allowing a user to select which data sources to utilize in reviewing the symptom data. Further, case selection and factors may be selected through a user interface. For example, according to at least one exemplary embodiment, in the glyphs displaying cats or dogs, one color may be assigned to gastro-intestinal syndromes, another color assigned to respiratory syndromes, a third color for eye inflammation syndromes, and so on. Finally, a selection window 460 allows the visual display of a selected statistical analysis of the data, and may allow a user to toggle between the primary geospatial display 405 and the selection window.

Example 2

Figure 4A:
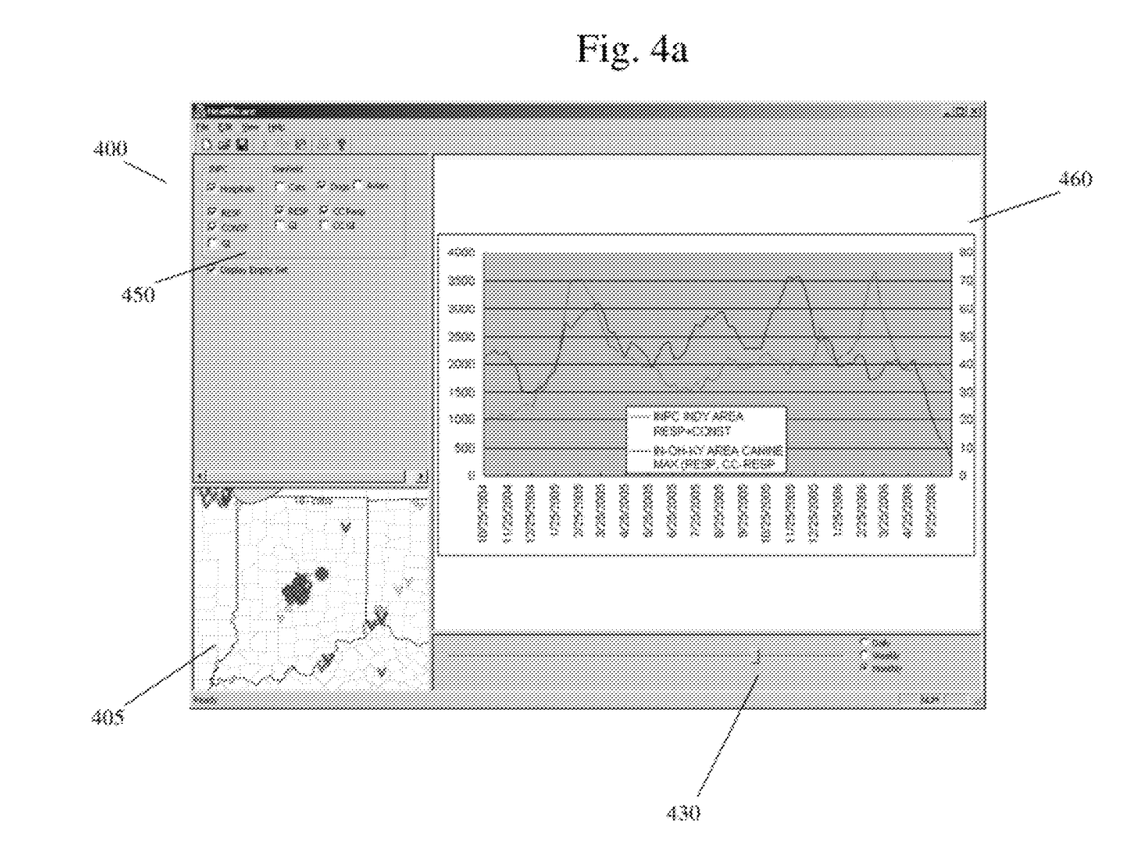

According to at least one exemplary embodiment, a case study of seasonal influenza in both humans and animals was studies utilizing at least one of the embodiments discussed above. By way of nonlimiting example, one or more databases accumulating symptom data from multiple emergency rooms within the Indianapolis metropolitan area, and one or more databases accumulating animal symptom data from multiple Banfield Pet Hospitals within the Indianapolis metropolitan area were utilized to accumulate respiratory syndromes reported in humans, dogs, and cats. FIG. 4a displays the temporally varying window centered over the Indianapolis metropolitan area relating to the relevant data for humans and canines during a multi-year period from October, 2004 through April, 2006. As will be appreciated, STL analysis was further utilized to determine if correlations between dog respiratory syndromes and human respiratory syndromes exist. Through the use of at least one embodiment outlined above, and utilizing the STL analysis coupled with one or more of the temporal and geospatial analysis methods outlined above, it was identified that respiratory symptoms occur in dogs approximately ten (10) days before humans in typical years. As such, the use of at least one methodology outlined above, coupled with real-time collection of data of dog symptoms provides a predictor of influenza in human populations for geographic areas going forward.

Example 3

In yet another nonlimiting exemplary embodiment, the effects of industrial wastewater release was studied through companion animal surveillance. In particular, three syndromes were identified as being potential indicators of adverse effects due to industrial wastewater release: eye inflammation, respiratory symptoms, and gastrointestinal symptoms. A geographical area was defined within an approximately 20 mile radius of a known spill, and companion animal data reported from Banfield Pet Hospitals was analyzed during a temporal range before and after the spill. Due to data sparsity related to eye inflammation reports, a bootstrapping analysis as described above was performed upon identifying a relevant time and geographic area. The results of the bootstrapping analysis are shown in Table 1, and indicate that eye-inflammation in dogs was significant near the wastewater release during the time period of interest, allowing health officials to predetermine potential adverse effects in humans.

TABLE 1

| species | statistic | eye inflammation |
|---|---|---|
| canine | mean 10% quantile before | 8.035 |
| | 10% quantile during | 2.365 |
| | 1-sided bootstrap p-value | 0.006 |
| feline | mean 10% quantile before | 11.195 |
| | 10% quantile during | 17.531 |
| | 1-sided bootstrap p-value | 0.909 |

It will be appreciated that the above-described embodiments are merely exemplary, and that those of ordinary skill in the art may readily devise their own implementations that incorporate the principles of the present invention and fall within the spirit and scope thereof.

What is claimed is:

1. A computer implemented method carried out by a computer executing instructions stored on a computer readable medium, the instructions comprising:
    obtaining, with the computer, a first data regarding patient symptoms for a non-human species, the first data comprising reported symptom incidences for the non-human specifies from a plurality of locations and stored on the computer;
    generating and storing a total value of symptom incidences for a select time period for each of the plurality of locations based on the stored first data with the computer;
    generating and storing a transform value for each of the plurality of locations by performing a power transform on the total value for each of the plurality of locations with the computer;
    generating with the computer, for each site of the plurality of locations a glyph having a visual characteristic that is dependent upon the stored transform value for the site;
    generating at least one CUSUM value with the computer, based on the stored first data;
    generating computer display information based on the at least one CUSUM value within the computer; and
    displaying the generated information on a display device in communication with the computer.

2. The computer implemented method of claim 1, wherein the step of generating and storing the transform value with the computer includes taking the square root of a sum of the total value for a site plus one.

3. The computer implemented method of claim 2, wherein the step of generating the glyph with the computer includes selecting a color of the glyph based on the transform value for the site.

4. The computer implemented method of claim 2, wherein the step of generating the glyph with the computer includes selecting a size of the glyph based on the transform value for the site.

5. A computer implemented method carried out by a computer executing instructions stored on a computer readable medium, the instructions comprising:
    obtaining, with the computer, a first data regarding patient symptoms for a non-human species, the first data comprising reported symptom incidences for the non-human specifies from a plurality of locations and stored on the computer;
    generating and storing a total value of symptom incidences for a select time period for each of the plurality of locations based on the stored first data with the computer;
    generating and storing a transform value for each of the plurality of locations by performing a power transform on the total value for each of the plurality of locations with the computer;
    generating with the computer, for each site of the plurality of locations a glyph having a visual characteristic that is dependent upon the stored transform value for the site;
    generating and storing quantile measures based on a select epicenter and time window with the computer;
    generating computer display information representative of the quantile measures with the computer; and
    displaying the generated information on a display device in communication with the computer.

6. The computer implemented method of claim 5, wherein the step of generating and storing the transform value with the computer includes taking the square root of a sum of the total value for a site plus one.

7. The computer implemented method of claim 6, wherein the step of generating the glyph with the computer includes selecting a color of the glyph based on the transform value for the site.

8. The computer implemented method of claim 6, wherein the step of generating the glyph with the computer includes selecting a size of the glyph based on the transform value for the site.

9. A computer implemented method carried out by a computer executing instructions stored on a computer readable medium, the instructions comprising:
    obtaining, with the computer, a first data regarding patient symptoms for a non-human species, the first data comprising reported symptom incidences for the non-human specifies from a plurality of locations and stored on the computer;
    generating and storing a total value of symptom incidences for a select time period for each of the plurality of locations based on the stored first data with the computer;
    generating and storing a transform value for each of the plurality of locations by performing a power transform on the total value for each of the plurality of locations with the computer;
    generating with the computer, for each site of the plurality of locations a glyph having a visual characteristic that is dependent upon the stored transform value for the site;

performing, with the computer, at least one bootstrapping analysis based upon the first data;

generating computer display information based upon the at least one bootstrapping analysis; and displaying the generated information on a display device in communication with the computer.

10. The computer implemented method of claim 9, wherein the step of generating and storing the transform value with the computer includes taking the square root of a sum of the total value for a site plus one.

11. The computer implemented method of claim 10, wherein the step of generating the glyph with the computer includes selecting a color of the glyph based on the transform value for the site.

12. The computer implemented method of claim 10, wherein the step of generating the glyph with the computer includes selecting a size of the glyph based on the transform value for the site.

* * * * *